(12) United States Patent  
Limon (10) Patent No.: US 7,316,709 B2
(45) Date of Patent: Jan. 8, 2008

(54) BALLOON CATHETER HAVING A TEXTURED MEMBER FOR ENHANCING BALLOON OR STENT RETENTION

(75) Inventor: Timothy A. Limon, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 688 days.

(21) Appl. No.: 10/756,730

(22) Filed: Jan. 13, 2004

(65) Prior Publication Data

US 2005/0154440 A1    Jul. 14, 2005

(51) Int. Cl.
*A61F 2/06* (2006.01)
(52) U.S. Cl. ...................................... 623/1.11; 600/585
(58) Field of Classification Search ............... 623/1.11, 623/1.12, 1.15; 606/191, 192, 194, 198; 600/434, 585
See application file for complete search history.

(56) References Cited

U.S. PATENT DOCUMENTS

| 5,108,416 | A | | 4/1992 | Ryan et al. |
| 5,180,367 | A | | 1/1993 | Kontos et al. |
| 5,196,024 | A | | 3/1993 | Barath |
| 5,250,070 | A | | 10/1993 | Parodi |
| 5,357,978 | A | | 10/1994 | Turk |
| 5,383,853 | A | * | 1/1995 | Jung et al. ............. 604/103.04 |
| 5,395,332 | A | | 3/1995 | Ressemann et al. |
| 5,505,702 | A | | 4/1996 | Arney |
| 5,571,087 | A | | 11/1996 | Ressemann et al. |
| 5,575,771 | A | | 11/1996 | Walinsky |
| 5,628,746 | A | | 5/1997 | Clayman |
| 5,649,941 | A | | 7/1997 | Lary |
| 5,653,690 | A | | 8/1997 | Booth et al. |
| 5,669,880 | A | | 9/1997 | Solar |
| 5,674,241 | A | | 10/1997 | Bley et al. |
| 5,797,935 | A | | 8/1998 | Barath |
| RE36,104 | E | | 2/1999 | Solar |
| 5,921,958 | A | | 7/1999 | Ressemann et al. |
| 5,954,740 | A | | 9/1999 | Ravenscroft et al. |
| 6,071,285 | A | * | 6/2000 | Lashinski et al. .......... 623/1.11 |
| 6,221,090 | B1 | | 4/2001 | Wilson |
| 6,394,995 | B1 | | 5/2002 | Solar et al. |
| 6,409,751 | B1 | | 6/2002 | Hall et al. |
| 6,447,501 | B1 | | 9/2002 | Solar et al. |
| 6,540,693 | B2 | | 4/2003 | Burbank et al. |
| 6,544,219 | B2 | | 4/2003 | Happ |
| 6,562,062 | B2 | | 5/2003 | Jenusaitis et al. |
| 6,569,192 | B1 | | 5/2003 | Foreman et al. |

(Continued)

FOREIGN PATENT DOCUMENTS

EP        0 834 293 A1    4/1998

(Continued)

*Primary Examiner*—Kevin T. Truong
(74) *Attorney, Agent, or Firm*—Fulwider Patton LLP (57) ABSTRACT

This invention is directed to a balloon catheter having at least one advancement wire with a distal end section secured to a distal tip section of the catheter, and with a textured section extending along the outer surface of at least a portion of an inflatable section of the catheter balloon. The textured section of the advancement wire preferably improves the ability of the balloon to remain in position in the patient's body lumen during inflation of the balloon to perform a medical procedure such as balloon angioplasty or stent touch-up.

17 Claims, 5 Drawing Sheets

U.S. PATENT DOCUMENTS

| | | |
|---|---|---|
| 6,740,104 B1 | 5/2004 | Solar |
| 2002/0010489 A1 | 1/2002 | Grayzel et al. |
| 2003/0018376 A1 | 1/2003 | Solar et al. |
| 2003/0144683 A1 | 7/2003 | Sirhan et al. |
| 2003/0204238 A1 | 10/2003 | Tedeschi |
| 2005/0085845 A1 | 4/2005 | Hilaire et al. |

FOREIGN PATENT DOCUMENTS

| | | |
|---|---|---|
| EP | 1 008 363 A2 | 11/1999 |

* cited by examiner

BALLOON CATHETER HAVING A TEXTURED MEMBER FOR ENHANCING BALLOON OR STENT RETENTION

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion.

An essential step in effectively performing a PTCA procedure is properly positioning the balloon catheter at a desired location within the coronary artery. To properly position the balloon at the stenosed region, the catheter must have good pushability (i.e., ability to transmit force along the length of the catheter) and flexibility to be readily advanceable within the tortuous anatomy of the patient's vasculature. Conventional balloon catheters for intravascular procedures, such as angioplasty and stent delivery, frequently have relatively a stiff proximal shaft section to facilitate advancement of the catheter within the patient's body lumen and a relatively flexible distal shaft section to facilitate passage through tortuous anatomy such as distal coronary and neurological arteries without damage to the luminal wall. To facilitate advancement of the catheter within the tortuous vasculature, conventional balloon catheters frequently have a lubricious coating on at least a portion of an outer surface of the catheter. However, one difficulty has been the tendency of the balloon to slip out of position during inflation of the balloon, a problem referred to as "watermelon seeding". Accordingly, it would be a significant advance to provide a catheter balloon with improved ability to remain in position during inflation, without inhibiting catheter performance characteristics such as catheter advanceability within the patient's vasculature.

INVENTION SUMMARY

The invention is directed to a balloon catheter having at least one advancement wire with a distal end section secured to a distal tip section of the catheter, and with a textured section extending along the outer surface of at least a portion of an inflatable section of the catheter balloon. The textured section of the advancement wire preferably improves the ability of the balloon to remain in position in the patient's body lumen during inflation of the balloon to perform a medical procedure such as balloon angioplasty or stent touch-up.

The catheter of the invention typically comprises an elongated shaft having a proximal end, a distal end, an inflation lumen, and a tubular member defining a guidewire lumen configured to slidably receive a guidewire therein. A balloon is secured to the shaft so that an inflatable interior of the balloon is in fluid communication with the inflation lumen. At least one advancement wire has a distal end section secured to a distal tip section of the catheter, a proximal end section at a proximal end section of the catheter, and a textured section extending at least along the outer surface of at least a portion of the inflatable section of the balloon and external to the guidewire lumen. During positioning of the catheter in a patient's body lumen the catheter is advanced with a guidewire slidably disposed in the guidewire lumen, and the advancement wire preferably enhances the pushability of the catheter to facilitate the advancement of the catheter in the patient's body lumen. In one presently preferred embodiment, the guidewire extends external to the balloon, with the guidewire lumen being a distal tip lumen having a proximal end located distal to the distal end of the inflation lumen. However, a variety of suitable configurations can be used for the guidewire lumen.

The textured section of the advancement wire generally comprises intermittent projections or peaks, producing a varied outer diameter along the textured section of the advancement wire. In one embodiment, the advancement wire comprises a core member, and the textured section of the advancement wire is formed by one or more projections which project from an outer surface of the core member, so that the projections extend at least in part away from the balloon outer surface. In one presently preferred embodiment, the one or more projections comprise a wire member wound on the outer surface of the core member. However, the textured section can be formed by a variety of suitable designs including intermittent spaced apart bands or band-like projections, a roughened outer surface of the advancement wire, or the peaks of an undulating surface of the advancement wire.

With the advancement wire extending external to the catheter balloon, the textured section is exposed along the outer surface of the balloon, to thereby enhance the frictional engagement of the balloon against the vessel wall during inflation of the balloon to dilate a stenosis. As a result, any tendency of the balloon to slip out of position in the patient's body lumen is prevented or inhibited by the catheter of the invention. Additionally, the textured section provides improved control over the dissection of a stenosis as the balloon inflates against the stenosis. Specifically, the textured section provides focal stresses as it cuts into the stenosis, thereby controlling the resulting dissection planes. However, unlike a cutting balloon having a blade along the outer surface of the balloon, the texture section in a presently preferred embodiment has a rounded outer surface which avoids substantial areas of injury to the vessel as the catheter is positioned therein. Additionally, the textured section provides regions of high and low stress which in one embodiment limits vessel damage to only the high stress areas.

In one embodiment in which the balloon is inflated within a previously expanded stent, the textured section is configured to mesh with the stent. Specifically, the longitudinally spaced apart projections or peaks of the textured section have a spacing therebetween which is configured to accommodate the stent struts. For example, with a conventional stent design comprising a series of connected rings, the stent strut forming a ring fits within the longitudinal space between adjacent projections or peaks of the textured section. Thus, during dilatation of a stenosed region within a previously implanted stent (typically referred to as "in-stent restenosis"), or during a stent touch-up in which the balloon further expands a partially expanded stent in the patient's body lumen, the balloon catheter of the invention does not slip longitudinally out of position during inflation of the balloon, due to the textured section of the advancement wire. It is important to match the length of the inflated balloon to the length of the stent in such procedures, to avoid unintended injury to the patient's vessel which can result when sections of the balloon over-inflate against the vessel wall. As a result, the balloon catheter of the invention prevents or inhibits such injury by inhibiting an otherwise well matched balloon from longitudinally slipping out of position within the stent during inflation of the balloon.

In an alternative embodiment in which the balloon catheter is a stent delivery catheter, the longitudinally spaced apart projections or peaks of the textured section have a spacing therebetween which is configured to mesh with a stent mounted on the balloon for delivery and deployment within the body lumen. Consequently, longitudinal movement of the stent on the balloon is prevented or inhibited by the textured section meshed with the stent, to preferably improve retention of the stent on the balloon during advancement of the catheter and inflation of the balloon. However, the textured section preferably provides no resistance to deflation of the inflation balloon or release of the stent from the balloon as the balloon is deflated to leave the stent implanted in the body lumen. Thus, with the stent and texture section meshed together, longitudinal movement of the stent on the balloon catheter is substantially prevented or inhibited such that the stent position on the balloon is not significantly altered, whereas radial retraction of the balloon and advancement wire from the expanded stent is unaffected by the advancement wire. The balloon catheter of the invention can be used with a variety of commercially available stents. Details regarding stent designs can be found in for example, U.S. Pat. No. 5,507,768 (Lau, et al.), incorporated herein by reference in its entirety.

In the embodiment in which the textured section is formed by a wound wire member, characteristics such as the pitch of the wound wire can be easily selected and manufactured to mesh with any of a variety of commercially available stents. The stiffness resulting from the wound wire will increase as the pitch of the wound wire decreases. Consequently, in one embodiment in which the pitch of the wound wire is relatively low, the wound wire is preferably formed of a relatively flexible material such as a polymer or a superelastic material such as NiTi alloy (Nitinol), to mitigate the increased stiffness that would otherwise result from the low pitch wound wire formed of a less flexible material such as stainless steel.

In a dilatation procedure, the balloon catheter of the invention has excellent balloon retention as the balloon is inflated, due to the textured section of the advancement wire. Additionally, the textured section contacting the lesion produces focal stresses providing improved control over the resulting dissection planes. In the embodiment in which a stent is around an outer surface of the balloon (i.e., a stent mounted on the balloon for delivery and deployment within the body lumen, or a previously expanded stent during a stent touch-up procedure or an in-stent restenosis dilatation procedure), the textured section provides improved balloon retention due to the meshing of the stent and the textured section, and without disadvantageously inhibiting retraction of the balloon away from the stent as the balloon is deflated. These and other advantages of the invention will become more apparent from the following detailed description and exemplary drawings.

DETAILED DESCRIPTION OF THE PREFERRED EMBODIMENTS

Figure 1:
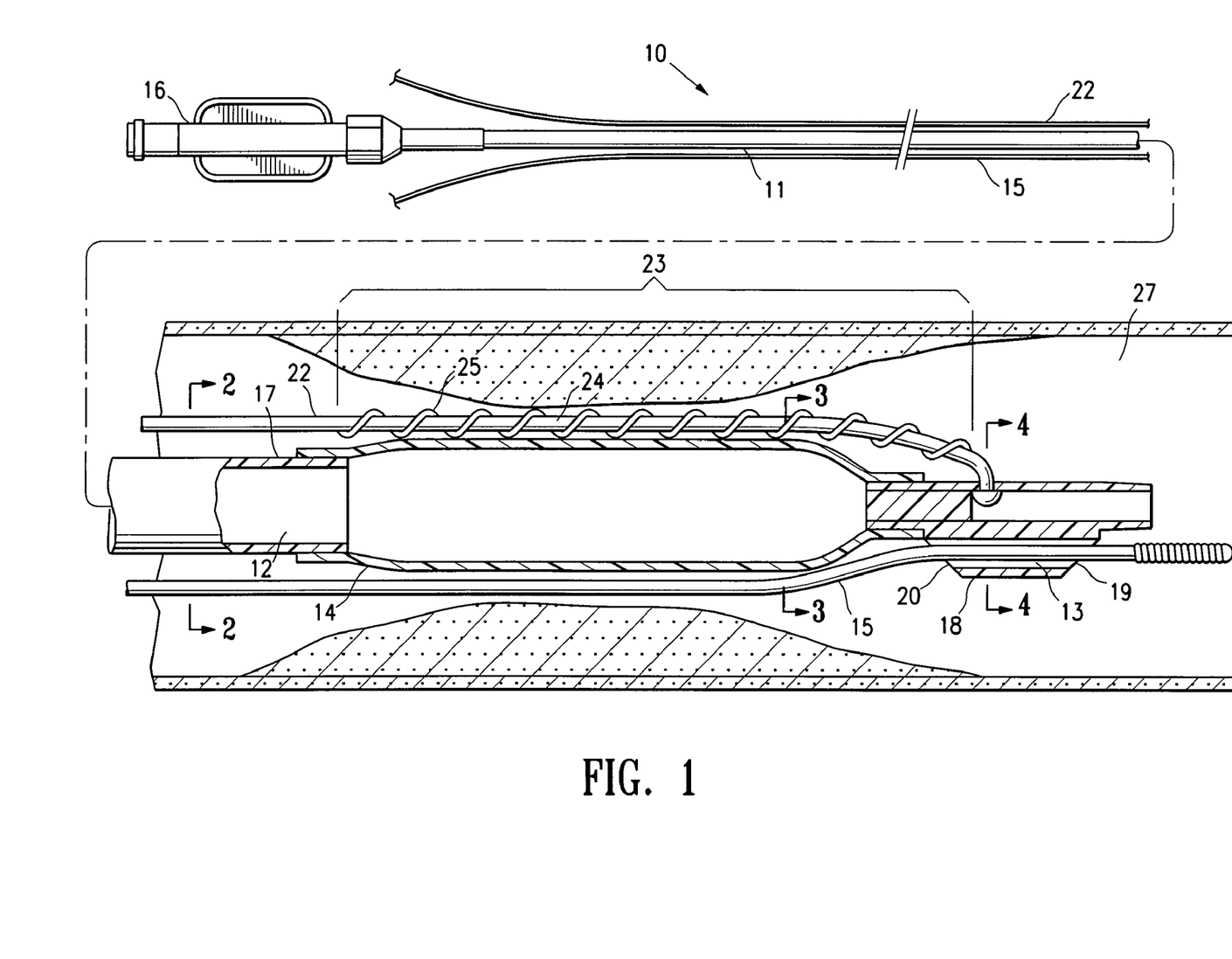
FIG. 1 is an elevational view, partially in section, of a rapid exchange type balloon catheter which embodies features of the invention.
Figure 2:
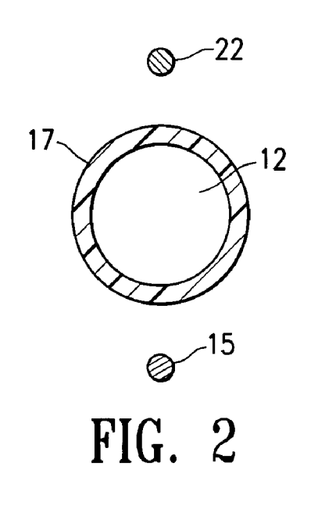
FIGS. 2-4 are transverse cross sectional views of the catheter shown in FIG. 1, taken along lines 2-2, 3-3, and 4-4, respectively.
Figure 3:
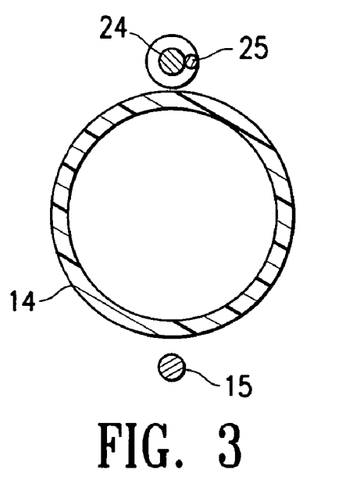
Figure 4:
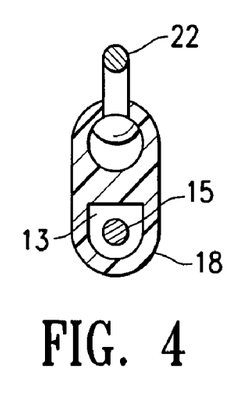

FIG. 1 illustrates a rapid exchange type balloon catheter 10, generally comprising a shaft 11 with an inflation lumen 12, a guidewire lumen 13 in a distal shaft section configured to slidingly receive a guidewire 15, and a balloon 14 on the distal shaft section. An adapter 16 at the proximal end of catheter shaft 11 is configured to direct inflation fluid into inflation lumen 12, to thereby inflate the balloon 14. FIG. 1 illustrates the balloon 14 in a low profile configuration prior to inflation, for introduction and advancement within the patient's body lumen 27. In use, the distal end of catheter 10 is advanced to a desired region of the patient's body lumen 27 in a conventional manner either over previously positioned guidewire 15, or with guidewire 15 already in the catheter 10. The balloon 14 is inflated to perform a procedure such as dilating a stenosed region of the body lumen, or expanding a stent as discussed in more detail in relation to the embodiment of FIG. 7, and the balloon deflated for removal of the catheter 10 from the body lumen. FIGS. 2-4 illustrate transverse cross sectional view of the catheter of FIG. 1, taken along lines 2-2, 3-3, and 4-4, respectively.

In the embodiment of FIG. 1, the shaft 11 comprises a first tubular member 17 defining the inflation lumen 12, and a second tubular member 18 defining the guidewire lumen 13 extending from a guidewire distal port 19 in a distal end portion of the catheter shaft to a guidewire proximal port 20 spaced distally from the proximal end of the catheter shaft. Inflatable balloon 14 has a proximal skirt section sealingly secured to the distal end of first tubular member 17, a distal skirt section sealingly secured to the second tubular member 18, and an inflatable cylindrical working length section therebetween, so that its interior is in fluid communication with inflation lumen 12.

Figure 5:
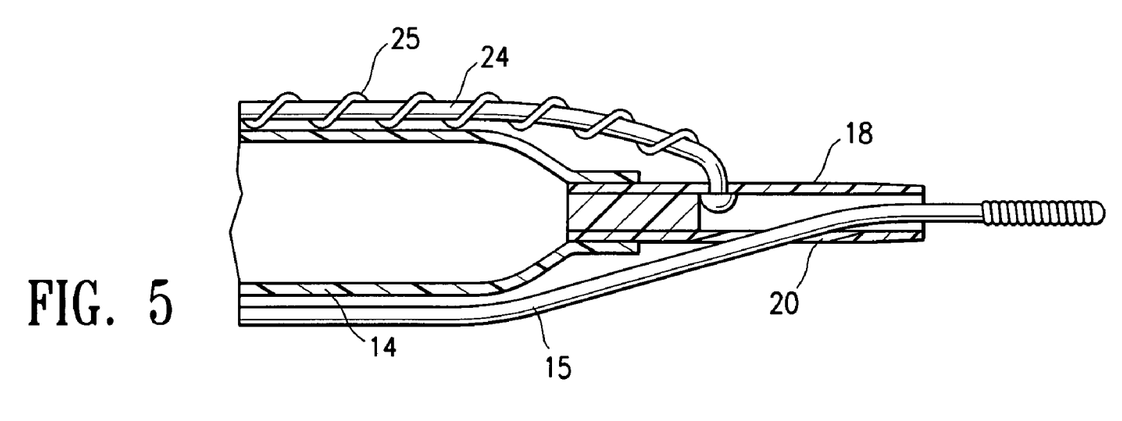
FIG. 5 illustrates an alternative embodiment of the catheter of FIG. 1, having the guidewire proximal port extending through a sidewall of the shaft.

In the embodiment of FIG. 1, the guidewire lumen 13 is a distal tip lumen having a proximal end located distal to the inflatable section of the balloon 14. However, a variety of suitable guidewire lumen configurations can be used. For example, the second tubular member 18 forming the guidewire lumen can extend further proximally than in the embodiment of FIG. 1 along some or all of the length of the balloon to any location along the length of the catheter 10. In an alternative embodiment, the guidewire proximal port 20 can extend through the sidewall of the second tubular member 18, as for example in the embodiment illustrated in FIG. 5. Additionally, the tubular member defining the guidewire lumen (i.e., the second tubular member) can alternatively extend within a distal section of the lumen of the first tubular member 17 and through the interior of the balloon 14, as is conventionally known for rapid exchange catheter designs. Although illustrated as one-piece tubular members, it should be understood that the first and second tubular members 17, 18 may be formed of multiple tubular members or multilayered tubular members. For example, in one embodiment, the first tubular member 17 comprises two or more tubular members joined end to end, to provide increasing flexibility distally along the length of the catheter.

An advancement wire 22 has a distal end secured to a distal tip section of the catheter, a proximal end section at the proximal end of the catheter shaft, and a textured section 23 along the outer surface of the balloon 14. In the embodiment of FIG. 1, the textured section 23 extends from the distal end of the advancement wire to a point on the advancement wire located at about the proximal end of the inflatable section of the balloon. However, in alternative embodiments, the length of the textured section 23 can be shorter or longer than the embodiment of FIG. 1, although the textured section 23 typically extends at least along the central cylindrical working length section of the balloon 14. For example, in one embodiment (not shown), the textured section 23 has a length about equal to the length of the inflatable cylindrical working length section of the balloon 14.

The textured section 23 extends externally of the guidewire lumen 13 and is exposed on the outer surface of the balloon 14. In an embodiment in which the balloon has folded wings (not shown) wrapped around the balloon in the low profile noninflated configuration prior to inflation of the balloon, the advancement wire is preferably outside the folds created by the wrapped wings, on the outer-most surface of the folded balloon.

In the embodiment of FIG. 1, the advancement wire comprises a core member 24 having a wire member 25 wound on the outer surface of the core member 24 to form textured section 23. Although discussed below primarily in terms of the embodiment in which the textured section comprises wire member 25, it should be understood that a variety of suitable texturing can be used to form the textured section 23. The wire member 25 is typically secured to the core wire only at the proximal and distal ends of the wire member 25, although it may alternatively be attached along the entire length of the wire member 25 or one or more sections thereof. The core member 24 and wire member 25 are preferably formed of solid wires. However, a hollow tube can alternatively be used to form all or part of the core member 24 and/or wire member 25. In one embodiment, the advancement wire core member 24 is formed of a commercially available guidewire, modified to provide the textured section 23 in accordance with the invention. The rounded outer surfaces of the core member 24 and wire member 25, best illustrated in FIG. 3, preferably provide a relatively atraumatic surface during positioning of the balloon catheter 10 in the patient's body lumen, despite being exposed on an outer surface of the balloon 14.

Figure 6:
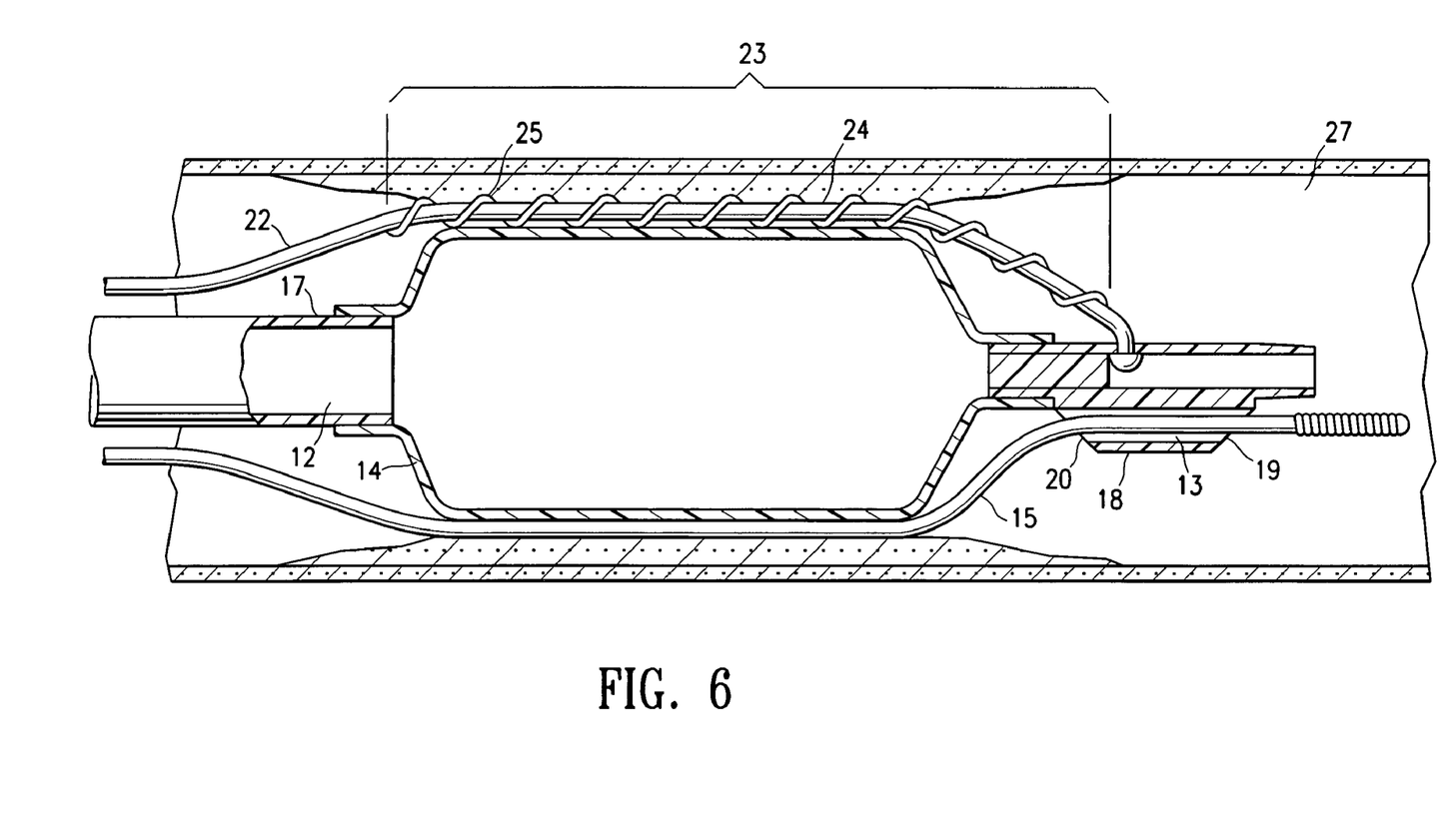
FIG. 6 illustrates the balloon catheter of FIG. 1, with the balloon inflated in a patient's body lumen to dilate a stenosed region of the body lumen.

FIG. 6 illustrates the balloon catheter of FIG. 1, with the balloon fully inflated, so that the balloon cylindrical working section contacts and dilates the stenotic region. The sections of the advancement wire 22 and the guidewire 15 extending along the outer surface of the balloon contact the stenosed section of the blood vessel during inflation of the balloon. As a result, the advancement wire 22 and the guidewire 15 frictionally engage the blood vessel wall, so that the balloon has an insubstantial amount of longitudinal slippage proximally or distally from the desired position in the blood vessel 27. The balloon 14 is then deflated, and the balloon catheter 10 can be withdrawn proximally over the guidewire 15 leaving the guidewire 15 in place, or withdrawn with the guidewire 15.

In the illustrated embodiment, the advancement wire 22 extends external to the entire length catheter shaft proximal of the balloon 14 (i.e., external to the entire length of the outer tubular member 17). In an alternative embodiment (not shown), the advancement wire 22 extends within, and/or is preferably secured to, at least a portion of the catheter shaft proximal to the balloon, typically entering the shaft at a relatively short distance from the proximal end of the balloon 14 so that it extends within a substantial portion, e.g., 70%-95%, of the length of the first tubular member 17. For example, in alternative embodiment, the advancement wire 22 is embedded in the wall of the first tubular member 17, or secured to an inner or outer surface thereof, or extends within a lumen in the first tubular member 17. In the embodiment of FIG. 1, the advancement wire 22 is typically not secured to the first tubular member 17, although it can alternatively be secured along all or part of the length of the first tubular member 17.

Figures 7, 8:
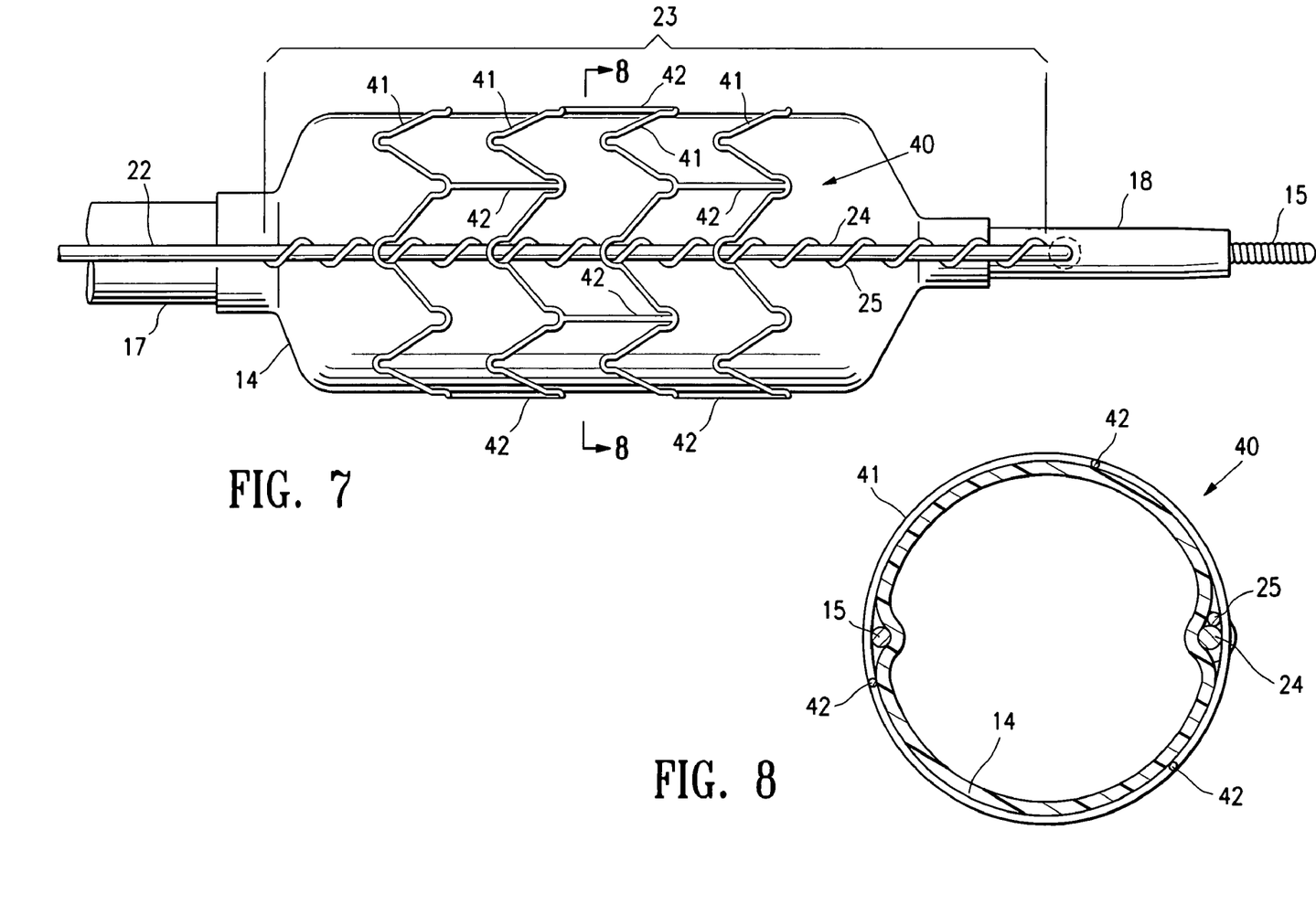
FIG. 7 illustrates top elevational view of the balloon catheter of FIG. 1, with the balloon in an inflated configuration within a stent in the patient's body lumen.
FIG. 8 is a transverse cross sectional view of the balloon catheter shown in FIG. 7, taken along line 8-8.

FIG. 7 illustrates a top elevational view of the balloon catheter of FIG. 1, with the balloon 14 inflated within a stent 40 in a patient's body lumen. The stent 40 typically comprises rings 41 longitudinally spaced apart and connected by links 42. In the illustrated embodiment, the rings 41 have a serpentine wave pattern of opposed turns which is transverse to the longitudinal axis of the stent, and the links connect adjacent rings. The pitch of the spiraling pattern of the wire member 25, the longitudinal spacing of the rings 41 of stent 40, and the size of the struts forming the stent rings are such as to allow the struts forming the rings of the stent 40 to fit in the space between adjacent projections formed by the wire member 25 of the advancement wire textured section 23. Thus, the stent 40 meshes with the textured section 23. FIG. 8 illustrates a transverse cross sectional view of the catheter of FIG. 7, taken along line 8-8. The height (i.e., diameter) of the advancement wire 22 along the textured section 23 is greater than the height of the struts forming the rings 41 of the stent 40 in the embodiment illustrated in FIG. 8, although it can alternatively be equal to or less than the height of the stent struts. A lubricious coating on the balloon 14 and/or a low rate of inflation of the balloon 14 preferably prevent the balloon 14 from being pinched between the textured section 23 and the stent struts. After inflation of the balloon 14 to perform a procedure such as a stent touch-up or dilatation in the case of in-stent restenosis, the balloon 14 is deflated, which retracts the textured section 23 of the advancement wire 22 radially inward away from the expanded stent 40, leaving the stent 40 implanted in the body lumen 27.

Figure 9:
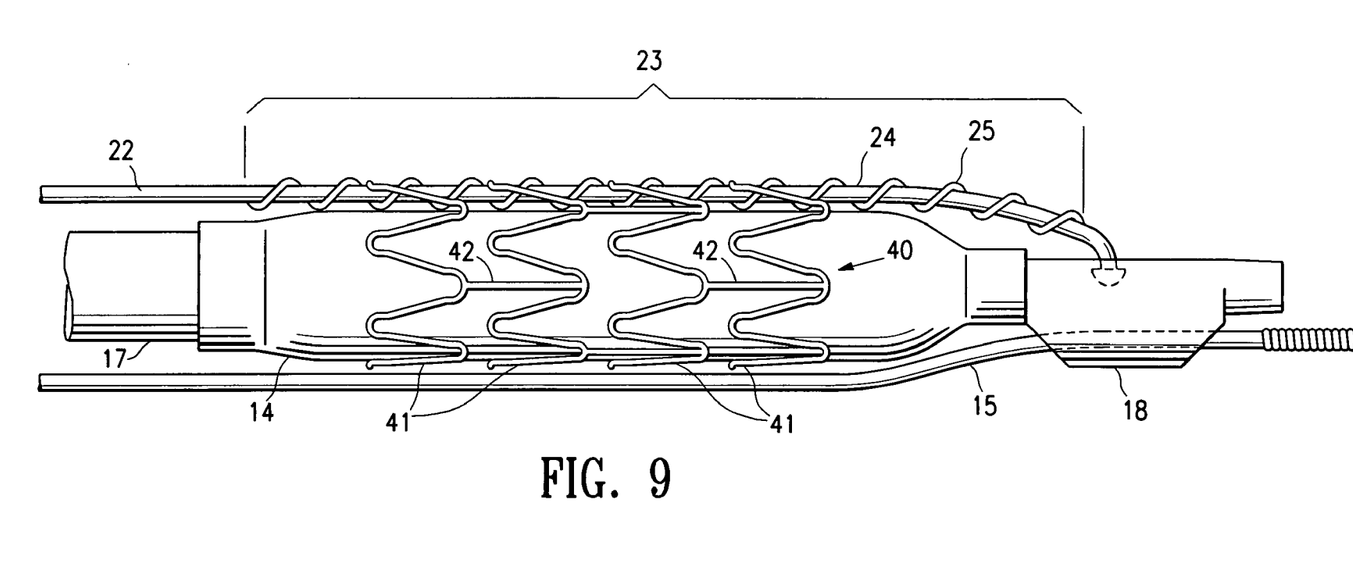
FIG. 9 illustrates a side elevational view of a stent delivery balloon catheter embodying features of the invention, with the balloon in a noninflated configuration with a stent mounted on the balloon

FIG. 9 illustrates an alternative embodiment, in which the catheter 10 is a stent delivery catheter with an unexpanded stent 40 mounted on the balloon for delivery and deployment within the body lumen 27. The rings 41 of the stent 40 are longitudinally spaced apart such that each ring strut fits between adjacent projections or peaks of the advancement wire 22, to thereby mesh the stent 40 with textured section 23 of the advancement wire 22.

Figure 10:
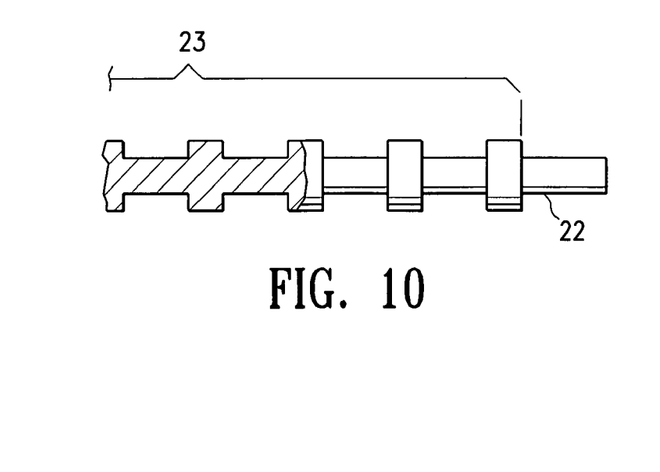
FIG. 10 is an elevational view of an alternative embodiment of the advancement member, having a texture section comprising band-like projection.
Figure 11:
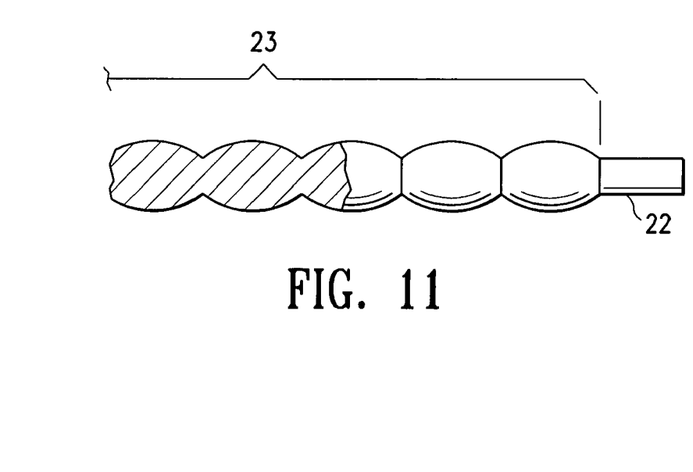
FIG. 11 is an elevational view of an alternative embodiment of the advancement member, having a textured section comprising peaks of an undulating surface of the core member.

Although the embodiments shown in FIGS. 1, 7 and 9 illustrate advancement wire textured section 23 comprising wire member 25, the textured section 23 can have a variety of suitable configuration. For example, FIG. 10 is an elevational view of an alternative embodiment of the advancement member 22, having a texture section 23 comprising band-like projections. The band-like projections are integral with the core member 24, formed for example by intermittently thinning the core member 24. Alternatively, the projections can be separate band members applied to the outer surface of the core member 24. FIG. 11 is an elevational view of an alternative embodiment of the advancement member 22, having a texture section 23 comprising peaks of an undulating surface of the core member.

To the extent not previously discussed herein, the various catheter components may be formed and joined by conventional materials and methods. Outer tubular member can be formed by conventional techniques, such as by extruding and necking materials found useful in intravascular catheters such a polyethylene, polyvinyl chloride, polyesters, polyamide, polyimides, polyurethanes, and composite materials. A variety of suitable conventional commercially available guidewires can be used for guidewire 15, which typically have a rounded outer surface and a coiled distal tip.

The length of the balloon catheter 10 is generally about 137 to about 145 centimeters, and typically about 140 centimeters for PTCA. The first tubular member 17 has an OD of about 0.017 to about 0.034 inch (0.43-0.87 mm), and an inner diameter (ID) of about 0.012 to about 0.022 inch (0.30-0.56 mm). The second tubular member 18 has an OD of about 0.017 to about 0.026 inch (0.43-0.66 mm), and an ID of about 0.015 to about 0.018 inch (0.38-0.46 mm) depending on the diameter of the guidewire 15 to be used with the catheter. The balloon 14 is typically about 8 to about 38 mm in length, with an inflated working diameter of about 1.5 to about 5 mm.

While the present invention has been described herein in terms of certain preferred embodiments, those skilled in the art will recognize that modifications and improvements may be made without departing from the scope of the invention. For example, in the embodiment of FIG. 1, the distal tip section of the catheter is formed by the second tubular member 18 of the shaft sealing secured to the distal skirt section of the balloon 14. However, a variety of suitable distal tip designs can be used including sealingly securing the distal skirt section of the balloon to itself and/or around the advancement wire 22, to seal off the distal end of the balloon 14 to allow for inflation of the balloon 14. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

I claim:

1. A balloon catheter, comprising:
   a) an elongated shaft having a proximal end, a distal end, an inflation lumen, and a tubular member defining a guidewire lumen configured to slidably receive a guidewire therein;
   b) a balloon secured to the shaft so that an inflatable interior of the balloon is in fluid communication with the inflation lumen, the balloon having an inflatable section and an outer surface; and
   c) at least one advancement wire having a distal end section secured to a distal tip section of the catheter, a proximal end section at a proximal end section of the catheter, and a textured section extending along the outer surface of at least a portion of the inflatable section of the balloon and external to the guidewire lumen, wherein the advancement wire comprises a core member, and the textured section of the advancement wire is formed by one or more projections which extend in a spiraling pattern longitudinally along an outer surface of the core member and which project from the outer surface of the core member at least in part away from the balloon outer surface, and the spiraling pattern spirals with a pitch which is configured to allow a strut of a ring of a stent around an outer surface of the balloon to fit between adjacent longitudinally spaced apart projections.

2. The balloon catheter of claim 1 wherein the one or more projections comprise a wire member wound on the outer surface of the core member.

3. The balloon catheter of claim 1 wherein the guidewire lumen extends at least along the distal tip section of the catheter located distal to the inflatable interior of the balloon.

4. The balloon catheter of claim 3 wherein the guidewire lumen is a distal tip lumen having a proximal end located distal to the distal end of the inflation lumen.

5. The balloon catheter of claim 3 wherein the inflation lumen is defined by an outer tubular member and the tubular member defining the guidewire lumen is an inner tubular member having a proximal section extending in the inflation lumen and a distal section extending through the balloon interior to a distal guidewire port in the distal end of the catheter.

6. The balloon catheter of claim 1 wherein the advancement wire distal end is secured to the tubular member defining the guidewire lumen.

7. The balloon catheter of claim 1 wherein the advancement wire extends external to the entire length of the catheter shaft proximal to the balloon.

8. The balloon catheter of claim 7 wherein the advancement wire is secured to at least a portion of the catheter shaft proximal to the balloon.

9. The balloon catheter of claim 1 wherein the advancement wire extends within and is secured to at least a portion of the catheter shaft proximal to the balloon.

10. The balloon catheter of claim 1 wherein the balloon has a folded noninflated configuration with wrapped wings, and the advancement wire extends outside folds created by the wrapped wings.

11. The balloon catheter of claim 1 wherein the catheter has 2 to 6 advancement wires.

12. A stent delivery balloon catheter, comprising:
   a) an elongated shaft having a proximal end, a distal end, an inflation lumen, and a tubular member defining a guidewire lumen configured to slidably receive a guidewire therein;
   b) a balloon secured to the shaft so that an inflatable interior of the balloon is in fluid communication with the inflation lumen, the balloon having an inflatable section and an outer surface;
   c) at least one advancement wire with a textured section formed by one or more projections or peaks on an outer surface thereof, the advancement wire having a distal end section secured to a distal tip section of the catheter, and a proximal end section at a proximal end section of the catheter, and the textured section extending along the outer surface of at least a portion of the inflatable section of the balloon and external to the guidewire lumen; and
   d) a stent mounted on the balloon, having rings longitudinally spaced apart, so that a strut of at least one of said rings is between adjacent projections or peaks of the advancement wire to thereby mesh the stent with textured section of the advancement wire.

13. The stent delivery catheter of claim 12 wherein the advancement wire comprises a core member and the one or more projections or peaks comprise a wire member wound in a spiraling pattern longitudinally along the outer surface of the core member.

14. The stent delivery catheter of claim 12 wherein the balloon has a folded noninflated configuration with wrapped wings, and the advancement wire extends outside folds created by the wrapped wings.

15. The stent delivery catheter of claim 12 wherein the one or more projections comprise intermittent spaced apart bands or band-like projections.

16. The stent delivery catheter of claim 12 wherein the texture section comprises peaks of an undulating surface of the advancement wire.

17. A stent delivery balloon catheter, comprising:
   a) an elongated shaft having a proximal end, a distal end, an inflation lumen, and a tubular member defining a guidewire lumen configured to slidably receive a guidewire therein;
   b) a balloon secured to the shaft so that an inflatable interior of the balloon is in fluid communication with the inflation lumen, the balloon having an inflatable section and an outer surface;
   c) at least one wire with a textured section formed by one or more projections or peaks on an outer surface thereof, the wire having a distal end section in a distal tip section of the catheter, and a proximal end section at a proximal end section of the catheter, and the textured section extending along the outer surface of at least a portion of the inflatable section of the balloon; and
   d) a stent mounted on the balloon, so that a strut of the stent is between adjacent projections or peaks of the wire to thereby mesh the stent with the textured section of the wire.

* * * * *